United States Patent [19]

Janes et al.

[11] Patent Number: 5,642,587
[45] Date of Patent: Jul. 1, 1997

[54] COMPRESSED DORMANCY PROCESS FOR INCREASED PLANT GROWTH

[75] Inventors: Harry W. Janes, Sayreville; Gerald E. Gore, North Branch; Wayne K. Wittman, Cranbury; Harry T. Roman, East Orange, all of N.J.

[73] Assignee: GRoW International Corp., North Branch, N.J.

[21] Appl. No.: 517,704

[22] Filed: Aug. 22, 1995

Related U.S. Application Data

[63] Continuation-in-part of Ser. No. 304,587, Sep. 12, 1994, abandoned, which is a continuation-in-part of Ser. No. 61,992, May 17, 1993, abandoned.

[51] Int. Cl.$^6$ .......................... A01G 7/00; A01G 23/00; A01H 7/00; A01H 3/02; C12P 17/02
[52] U.S. Cl. ...................... 47/58; 47/DIG. 3; 47/DIG. 6; 435/123
[58] Field of Search .................................. 47/58, DIG. 3, 47/DIG. 6; Plt./50.3; 435/123

[56] References Cited

PUBLICATIONS

Borman. Scientists mobilize to increase supply of anticancer drug taxol. C & EN. 11–18. Sep. 2, 1991.

Borman. Anticancer drug: Boost to taxol supply planned. C & EN. 4. Mar. 9, 1992.

Foster et al. Height and growth habit of Norway spruce rooted cuttings compared between two serial propagation cycles. Can. J. For. Res. 19:806–811. 1989.

Lumis and Johnson. Response of container-grown 'Hicks' Yew to preplant night lighting. HortSci. 18:438–439. 1983.

McGuire et al. Cold storage of rooted Taxus cuttings on subsequent summer regrowth. J. Environ. Hort. 9:36–37. 1991.

Wise et al. Propagation of *Abies fraseri* by semidormant hardwood stem cuttings. HortSci. 20:1065–1067. 1985.

*Primary Examiner*—David T. Fox
*Assistant Examiner*—Melissa L. Kimball
*Attorney, Agent, or Firm*—Ezra Sutton

[57] ABSTRACT

A method for accelerating the growth of *Taxus X media* 'Hicksii' and related Taxus species to enhance the production and recovery of taxol and Taxotere from plant tissues is described. The method includes the steps of increasing the production of biomass by cycling growth periods of Taxus plants within a greenhouse or other enclosed structure, harvests of plant parts and cold storage of the remaining unharvested plants to break dormancy and condition the plant for the next cycle of growth and harvest. After at least several cycles, entire plants are harvested for extraction from all plant parts while other plants are saved for stock plants or reforesting. The collected plant material is prepared for extraction of taxol or Taxotere, compounds used in the treatment of cancer.

19 Claims, 2 Drawing Sheets

PRUNING EFFECTS ON BUD DEVELOPMENT 8 WEEKS AFTER COLD TREATMENT

| MOUNT PRUNED | # OF BUDS GROWING | FRESH WEIGHT/BUD (gr.) |
|---|---|---|
| CURRENT YEARS GROWTH | 22.0 | 1.43 |
| 1/2 OF PREVIOUS YEAR'S GROWTH | 29.6 | 1.50 |
| ALL OF PREVIOUS YEAR'S GROWTH | 29.0 | 1.56 |
| NO PRUNING | 31.8 | 0.93 |

FIG. 1

COMPRESSED DORMANCY PROCESS FOR INCREASED PLANT GROWTH

RELATED APPLICATIONS

This application is a continuation-in-part of application Ser. No. 08/304,587, filed on Sep. 12, 1994, now abandoned, which is a continuation-in-part of application Ser. No. 08/061,992, filed on May 17, 1993, now abandoned.

I. FIELD OF THE INVENTION

This invention relates to the development of a compressed dormancy process for plants and thereby increasing the number of growth cycles in a typical growing season for increased biomass production, and in particular such plants as *Taxus* x *media* "Hicksii" and related Taxus species for increased biomass production for the ultimate purpose of Taxol extraction.

II. BACKGROUND OF THE INVENTION

In the United States alone, over 45,000 women die each year from breast cancer and over 100,000 people from lung cancer (1). Tens of thousands more die from other types of cancer. One of the few plant derived drugs that has shown quantitative proof of cancer treatment is Taxol. Taxol has been shown to be effective over a wide range of the most deadly forms of cancer, such as ovarian, lung and breast (2).

Over the last 30 years, the pharmaceutical industry has spent vast sums of money in an attempt to synthesize Taxol. Their efforts have not been successful nor have their results proven cost effective to-date even considering the many public relations announcements to the contrary.

Taxol is currently very expensive, approximately $6,000 per treatment (3). The reason for this is the short supply of raw material needed to manufacture the drug and the inability of research scientists to mass synthesize the drug.

Currently, the approved NCI-accepted method of Taxol production is from the bark of the Pacific Yew (4). This crude method requires approximately 10,000 pounds of biomass to produce approximately one pound of Taxol (5). This environmentally insensitive method of obtaining biomass for Taxol extraction is the current state-of-the-art now being employed.

With a "return to nature" trend taking hold and the desire by some people to seek plant related drugs for human ailments, another non-synthetic technology approach to the Taxol availability problem is possible.

As a result of the gross limitations discussed above, the inventors of this patent have developed a unique and commercial process to overcome the shortage of biomass needed for the extraction of Taxol. The plant growth system of the present invention incorporates two key components:

1. The present invention uses a widely grown commercially available plant variety *Taxus* x *media* "Hicksii". By substituting this variety for the Pacific Yew one can eliminate the need to cut and destroy the rare Pacific Yew from its natural environment which could lead to the elimination of this rare species.

2. The present invention relates to the development of a new technique that the inventors have coined as "Compressed Dormancy" and is employed to cycle the plant from a non-growing condition to an active growing condition a number of times during a typical growing season. This ability to cycle the plant from "on" to "off", produces up to five (5) times as much growth annually as that produced in a normal annual growing season. This method provides for an increase in the amount of biomass produced which is then harvested and processed into useful products, such as Taxol.

This is a unique commercial process for increasing the number of growth cycles of plants as the inventors have demonstrated on a type of Taxol bearing plant. The methodology is based on the desire of the inventors to produce large amounts of biomass suitable for the extraction of Taxol, and ultimately for the low cost treatment of cancer.

III. DESCRIPTION OF THE PRIOR ART

The use of Compressed Dormancy is a new concept. Plant dormancy is a normal process in nature that occurs on a yearly or seasonal cycle. Seasonal plant dormancy can be influenced by many factors such as temperature (both hot and cold), fire, light, and water. Some or all of these factors contribute to the condition of dormancy. The past practice or prior art of overcoming dormancy comes from the floriculture or horticulture industries.

Many commercial plant growers "force" or control dormancy in certain flower bulbs such as tulips and hyacinths (6) only once in a typical growing season. The common peach tree is another plant where the length of the dormant period can be altered by selective breeding. Typically, if bred for southern regions the amount of cold required for bud growth is less. Therefore, if planted in the North they will break dormancy too soon and will flower too early in the Spring when there still is a possibility for a late frost. If bred for northern regions and planted in the South, they might not break dormancy since there is not enough cold (degree and length) to break the dormancy.

In each of above cases and for other plants not listed, the prior practice is to control dormancy for the ultimate purpose of producing a flowering plant for ornamental purposes or for a specific day in the year or for producing a certain desired fruit or vegetable. In each case where dormancy plays a role, this flowering or fruit production cycle can only be done once a year.

The present invention differs in that it uses a unique cold temperature regimen as a mechanism to induce the plant to produce up to the equivalent of five (5) growing cycles which is equivalent of five years growth in just one year. This Compressed Dormancy and enhanced growing period relates to the biomass of the plant (needles, roots, stems, etc.) and not to the flowering parts.

IV. SUMMARY OF THE INVENTION

A. Our steps

We have discovered, and demonstrated through detailed experimentation, how to control and compress the dormancy cycle of the plant *Taxus* x *media* "Hicksii". The potential benefit from our discovery lies in the fact that one can produce more growth over a shorter period of time. Our method comprises the following steps of:

1. Compressing or shortening the plant dormancy cycle to allow for an increased number of growing cycles in a typical growing season plants such as *Taxus* x *media* "Hicksii".

2. Using a novel method of alternating cold and warm treatments in order for the plant to produce increased amounts of biomass not normally found in the growing cycle of the plant.

3. Producing up to five years of typical plant growth in just one year by use of our compressed dormancy technique.

B. Objectives

1. It is therefore the primary objective of this invention to produce more biomass over a given period of time using compressed dormancy in plants, especially as demonstrated in the plant *Taxus x media* "Hicksii" for the ultimate purpose of increased Taxol extraction.

2. It is also an object of the invention to employ this technique in other species of Taxus and in other plants.

3. Another object of the invention is to apply this process to any plant where dormancy plays a role in the life cycle of the plant. Other objects and advantages of the invention will become readily apparent from the ensuing description.

BRIEF DESCRIPTION OF THE DRAWINGS

FIG. 1 is a table of the pruning effects on bud development eight weeks after cold treatment.

V. DETAILED DESCRIPTION OF THE INVENTION

A. General Background

Figure 2:
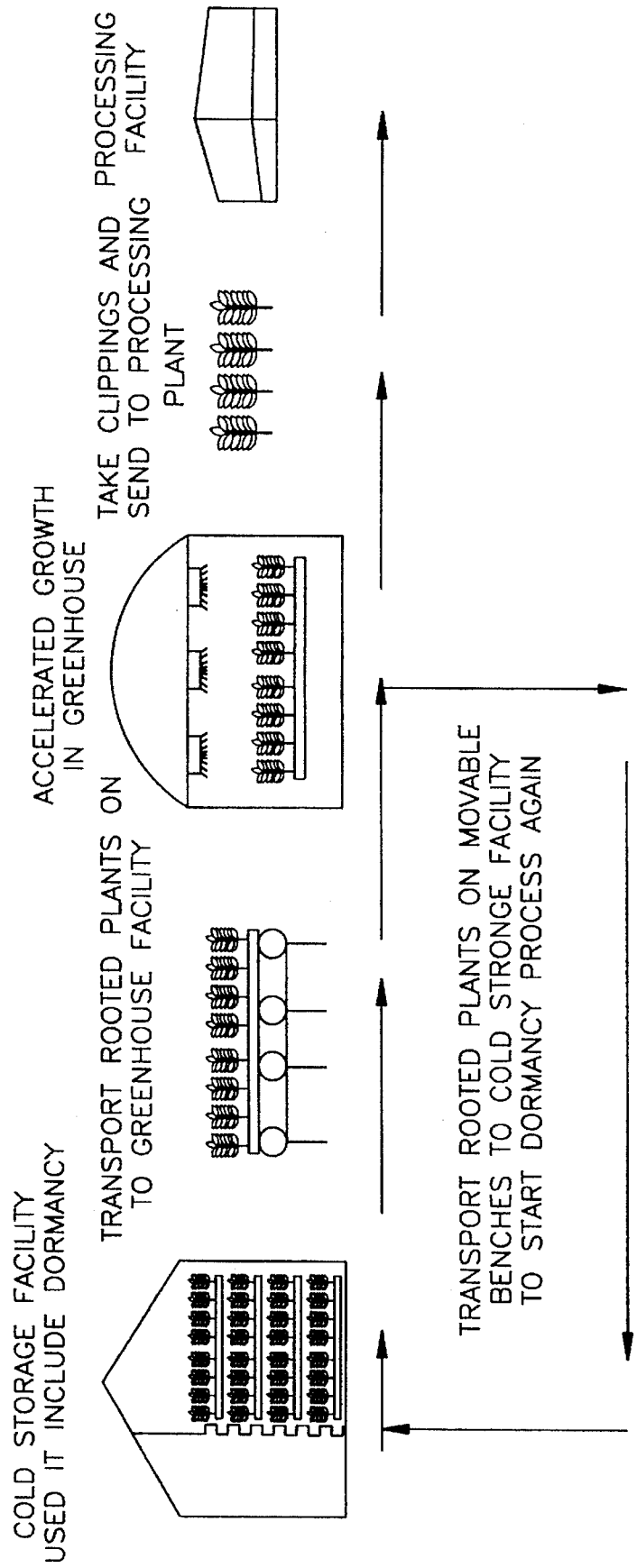
FIG. 2 illustrates the closed loop Compressed Dormancy Process.

The purpose of this invention was to define the requirements for the initiation and continued growth of *Taxus x media* "Hicksii" plants under controlled growing conditions. Any plant in this genus will follow the same pattern of growth after being exposed to our process.

Plants in the genus Taxus are generally winter hardy with dormancy being a natural part of the yearly growing cycle of the plant. Taxus species have in general a shorter growing season than deciduous trees and shrubs that grow throughout most of the summer months. After the period of active plant growth (mid-late summer), the plant goes into a dormant non-growing period and must be exposed to cold winter temperatures to break the dormant non-active growing period.

During the winter, the cold weather initiates the growth cycle by initiating certain chemical reactions within the plant that are a precursor to visible external growth. The plant stays in this pattern until temperatures and light levels rise in the spring (April to mid-June).

The plant then goes into an active growth period and produces a visible flush of new external growth from the previous year's buds located along the twigs of the plant. The plant then goes back into a non-active growing dormant cycle (mid-late summer) and the cycle is repeated. It must be pointed out that the cold temperatures of the winter months are necessary to break dormancy. Without experiencing this cold period the plant will not produce any new external growth. Herein we are defining a growth cycle as the period during which there is visible external growth.

Taxus will flourish in any light from full sunlight to partial shade. Taxus does best in well drained slightly acid fertile soil with an even supply of moisture. When not in the wild, fertilizer can be applied as little as once a growing season, using a 5-10-5 water soluble solution. These plants have a slow to medium growth rate, are highly resistant to diseases and pests, and are easily propagated.

The present invention recognizes that the dormancy cycle of various plants could be modified or adapted to meet a controlled growth cycle or growing regime. This growing cycle, as typically found in nature is limited to one growing cycle during a calendar year or growing season. By providing for such a growth regime, one could grow a plant under ideal growing conditions and produce "multiple ideal growing periods" within a year versus one growing period per year. The present invention demonstrated that this process produces more biomass per unit area and per unit of time (accelerated growth) thus resulting in the production of more Taxol than that found in the wild or other natural our-of-doors conditions.

B. Identification of Taxol

It has been generally believed that other species of Taxus contain Taxol. We specifically determined that authentic Taxol was present in the initial test plants of *Taxus x media* "Hicksii"that were to be used for all of our experimental work.

1. Methods and Materials

Day 1–Jul. 8, 1992: Take 1–10 grams of fresh needles from *Taxus x media* "Hicksii" test plants. Grind in liquid nitrogen with mortar and pestle until leaves are a fine powder. Place powder in a 100 ml flask. Add approximately 50 ml of 1:1 Methylene Chloride:Methanol (If using 1 gram of needles this is acceptable, slightly more solution is needed if using 10 grams of needles). Allow to shake overnight for 16 hours at 150 rpm.

Day 2-Jul. 9, 1992: Take flask off shaker. Filter off plant debris with vacuum using two filter papers washing off using Methanol. Take solvent and dry with a rotary evaporator. Take dried flask, rinse with methylene chloride and add solution to separatory funnel. Rinse flask with deionized distilled water and add solution to separatory funnel. Shake funnel and allow to settle for 15 minutes. Remove bottom, methylene chloride phase. Add fresh methylene chloride to funnel. Shake funnel again and allow to settle for 15 minutes. Remove bottom phase and add anhydrous sodium sulfate to it and transfer to rotary evaporative flask. Take methylene chloride phased and dry with rotary evaporator. Resuspend in approximately 5 ml methanol. Measure and record the final volume. Filter with 0.1 to 0.45 filter paper. Analyze with HPLC for Taxol.

2. Test Results

The following formula was used for calculating the % of Taxol:

extract peak area×weight of Taxol standard injected(ug) ×total extract volume(uL)×range used for the standard/ standard peak area/volume injected(mL)/total weight(ug)/ range used for the extract.

1. Extract peak area=166143
2. Weight of Taxol standard injected (ug)=2.5
3. Total extract volume (uL)=5000
4. Range used for the standard=0.01
5. Standard peak area=11291848
6. Volume injected (uL)=5
7. Total tissue weight (ug)=1000000
8. Range used for the extract=0.01

3. Conclusion

The results identified 0.003678384% or approximately 40 micrograms of authentic Taxol/gram of fresh *Taxus x media* "Hicksii" biomass. A second test run indicated 0.003479036% Taxol. It was concluded that authentic Taxol is present within the test plant group that were used in the Compressed Dormancy Process.

C. Compressed Dormancy Process

In order to develop this process a number of experiments were conducted from May 1993 until June 1994. These experiments were centered on the concept of controlling and compressing the dormancy cycle of *Taxus x media* "Hicksii".

The subject plants used in the following experiments were previously grown out-of-doors under cultivated field conditions for three years and were transplanted into two gallon pots using a mixture of peatmoss, vermiculite and perlite (Brand name Promix). The plants remained out-of-doors in the two gallon pots for approximately one year prior to the first experiment. Each plant was watered weekly and fed once a month a commercial brand water soluble fertilizer, consisting of a mix of 20% nitrogen, 20% phosphorus, and 20% potassium (Peters).

Approximately 50 *Taxus* x *media* "Hicksii" plants were thus selected for the experiments and placed within a greenhouse complex in May 1993. All experiments were conducted under controlled conditions using a cold chamber to break dormancy and a glass covered greenhouse for the main growing cycle.

Experiment 1: Methods and Materials

An observational experiment was conducted on twelve plants. This observational experiment was conducted during the time period of May 7, 1993 through Jun. 16, 1993. Twelve study plants were held in the cold chamber under the condition of no light, relative humidity of 85% and at a temperature of 38 degrees F for varied amounts of time (Three plants for 10 days, three plants for 20 days, three plants for 30 days and three plants for 40 days). This experiment was conducted to observe any abnormal growth characteristics.

Results of Experiment 1:

No visible increased in growth after 30 days of cold treatment.

Experiment 2: Methods and Materials

Experiment #2: The detailed experiment began on Nov. 23, 1993. The above 12 plants used in experiment #1 along with three new plants that had not previously seen any cold treatments (CT) were placed back into the cold chamber under the condition of no light, relative humidity of 85% and at a temperature of 38 degrees F. Three additional plants were used as a control and remained in the greenhouse under normal growing conditions. Each of the plants remained in the cold chamber under the cold conditions for 30 days. They were than removed and placed back into the greenhouse on Dec. 23, 1993 and grown under similar conditions. In all, 18 plants were used in experiment #2.

The study procedure followed and involved making weekly observations of the plants and recording the growth of eight selected buds on each plant. The selected plants were tagged, each with a different colored plastic string. Measurements of plant growth began in February of 1994 and continued through April of 1994. At the end of the study the tagged branches were pruned from the plant and weighed under both fresh and dried conditions.

Results of Experiment #2

1. Total average growth (in centimeters) observed for the 18 plants included:
   a. 3 plants with 30 Days CT and no previous CT=7.9
   b. 3 plants with 30 Days CT+10 days previous CT=12.0
   c. 3 plants with 30 Days CT+20 days previous CT=9.6
   d. 3 plants with 30 Days CT+30 days previous CT=13.2
   e. 3 plants with 30 Days CT+40 days previous CT=12.1
   f. 3 plants with no CT=2.1

Interpretation a vs f: The average growth increase per week of the CT plants vs the plants with no CT was 276%.

Interpretation b,c,d,e vs a: The average increase per week of the CT+previous CT plants vs the plants with just one CT was 22–67% with a median increase of 44%.

Interpretation b,c,d,e vs f: The average growth per week of the CT+previous CT plants vs the plants with no CT at all was 357–529% with a median increase of 443%.

2. Total average fresh weight (in grams) observed for the 18 plants included:
   a. 3 plants with 30 Days CT with no previous CT=1.6
   b. 3 plants with 30 Days CT+10 days previous CT=2.4
   c. 3 plants with 30 Days CT+20 days previous CT=1.7
   d. 3 plants with 30 Days CT+30 days previous CT=2.5
   e. 3 plants with 30 Days CT+40 days previous CT=3.1
   f. 3 plants with no CT=0.6

Interpretation a vs f: The average fresh weight increase per week of the CT plants vs the plants with no CT was 167%.

Interpretation b,c,d,e vs a: The average fresh weight increase per week of the CT+previous CT plants vs the plants with just one CT was 6–94% with a median increase of 50%.

Interpretation b,c,d,e vs f: The average fresh weight growth per week of the CT+previous CT plants vs the plants with no CT at all was 183–417% with a median increase of 234%.

3. Total average dry weight (in grams) observed for the 18 plants included:
   a. 3 plants with 30 Days CT with no pervious CT=0.5
   b. 3 plants with 30 Days CT+10 days previous CT=0.7
   c. 3 plants with 30 Days CT+20 days previous CT=0.5
   d. 3 plants with 30 Days CT+30 days previous CT=0.7
   e. 3 plants with 30 Days CT+40 days previous CT=0.9
   f. 3 plants with no CT=0.2

Interpretation a vs f: The average dry weight increase per week of the CT plants vs the plants with no CT was 150%.

Interpretation b,c,d,e vs a: The average dry weight increase per week of the CT+previous CT plants vs the plants with just one CT was 0–80% with a median increase of 40%.

Interpretation b,c,d,e vs f: The average dry weight growth per week of the CT+previous CT plants vs the plants with no CT at all was 150–350% with a median increase of 250%.

Conclusion from Experiment #2

1. The best average growth appeared on the plants which were exposed to 30 days of cold treatments plus a previous cold treatment.

2. The best average fresh weight increase appeared on the plants exposed to 40 days of cold treatments plus a previous cold treatment.

3. The best dry weight increase appeared on the plants which were exposed to 40 days of cold treatment plus a previous cold treatment.

4. In all cases including 1, 2, 3, above; the smallest increases were shown for 20 days of previous cold treatments.

5. There is a remarkable difference in growth rates between the plants exposed to no cold treatments and those receiving the cold treatments.

6. This demonstrated that the present invention promotes an increased rate of growth or accelerated growth.

Experiment 3: Methods and Materials

Experiment #3 was initiated on Feb. 22, 1994. Twenty plants from the original group that had not been subjected to any previous cold treatments or pruning were used in this experiment. The plants were divided into four groups of 5 plants each. Each group received a different amount of pruning. The pruning regimen included;
   a. No pruning of any growth,
   b. Pruning the current years growth which included all of soft wood to the semi-hard wood growth,
   c. Pruning ½ of the previous year's growth which included all of the soft wood and ½ semi-hard wood growth down to the hardwood growth,
   d. Pruning all of the previous year's growth including all of soft wood and semi-hard wood growth down to the hardwood growth.

After pruning, all 20 plants were placed in the cold chamber and held at 38 degrees Fahrenheit with a relative humidity of 85%. All plants were kept under no light conditions. Each of the plants remained under the cold conditions for 30 days. They were than removed and placed back into the greenhouse on Mar. 22, 1994 and grown under normal greenhouse conditions.

The study procedure followed and involved making weekly observations of the plants and recording the growth of selected buds on each plant. Observations of plant growth began on Mar. 22, 1994 and ended eight weeks later. At the end of the study, observations were noted and reported.

Results of Experiment #3

As seen in Experiment #2, dormancy was broken after 30 days of cold treatments. All plants exposed to cold treatments showed a marked increased in bud growth. All buds along the stems that were left were counted and weighed (See FIG. 1). Results of experiment #3 include;

a. No pruning of any growth: # of active buds growing= 31.8 with an average fresh weight/bud of 0.93 grams.

b. Current year's growth: # of active buds growing=22 with an average fresh weight/bud of 1.43 grams.

c. One half of the previous year's growth: # of active buds growing=29.6 with an average fresh weight/bud of 1.50 grams.

d. All of previous year's growth: # of active buds growing=29.0 with an average fresh weight/bud of 1.56 grams.

Conclusion from Experiment #3

1. Cold treatments break dormancy conditions and cause the plant to grow when placed in a heated greenhouse.

2. Dormancy can be broken at any time during the year by placing the plant in a cool storage area.

3. Plants subjected to pruning followed by cold treatments produced more growth and weight over those exposed to no cold treatments and pruning.

4. In all cases after the plants were pruned. The number of buds growing was less than that of the plants where no pruning occurred; however the fresh weight of the buds following pruning was at least 50% greater than that of the plants where no pruning occurred. See FIG. 1.

D. Overall Conclusion from Experiments 1–3

1. The compressed dormancy process is repeatable, thus leading to the conclusion that it is a predictable event that can be controlled.

2. Controlled cold treatments after an active growing period within a heated greenhouse will break dormancy and will enable the plant to grow again when placed back into heated greenhouse.

3. Pruning the plant in conjunction with cold treatments will produce a more robust developed bud and overall plant growth than no pruning.

4. Without cold treatments the plant would stop growing and not produce any more growth after a period of time.

VI. SIGNIFICANCE OF THE WORK

It is possible to implement a yearly controlled growing cycle which includes five (5) cold treatment exposures. Each exposure would involve 30 days of previous cold treatment plus 40 days in the greenhouse (70 days total treatment×5 exposures=350 days) This would result in significant increases in yearly growth (as much as 5 times the annual average), fresh weight, and dry weight yields of the plant. The significance of our work falls into five major areas;

A. Medical Applications

Taxol production: One current NCI-accepted method of Taxol production is from the bark of the Pacific Yew (*Taxus brevifolia*). This crude state-of-the-art method requires approximately 10,000 pounds of bark biomass to produce one pound of Taxol.

*Taxus* x *media* "Hicksii", which is a commercially grown ornamental variety, has been shown to produce Taxol. The needles of this plant have been collected and used as the biomass feedstock for the extraction of Taxol, an anti-cancer drug. The compressed dormancy process previously described incorporates a significant and novel approach to overcome the limits of the above currently accepted NCI method of Taxol extraction and would eliminate the need to use the Pacific Yew as the prime biomass source for the production of Taxol. It has been reported (8) that there is more Taxol available from *Taxus* x *media* "Hicksii" than from the bark of *Taxus brevifolia*.

B. Other Medical Drugs

The use of compressed dormancy could be applied to plants that go through an annual dormancy process. It is envisioned that numerous other plants with medical properties can be grown under this system.

C. Ornamental Horticulture Applications

*Taxus* x *media* "Hicksii", is one of the most widely used ornamental plants for landscaping. The use of our process would decrease the growing time of a plant thus providing for a salable plant in 2–3 years instead of 4–5 years. Other Taxus species should also benefit from our invention.

Many fruit bearing plants as well as ornamentals could benefit from this process. One could apply Compressed Dormancy, for example, to berry producing plants such as raspberries, blackberries etc. to shorten the time from rooted cutting to salable plant. This would greatly increase the yearly output of such plants, shorten the growing time, and increase profits of nursery owners.

D. Forestry Applications

The use of the Compressed Dormancy process could be applied in the production of tree seedlings used in the forestry industry here in the U.S. or elsewhere in the world. The technique would utilize selected evergreen varieties commonly used for lumber production. The plants would be grown under the Compressed Dormancy process and within one year, be transplanted back into the wild. Our process would cut the death rate from transplanting by producing a more mature robust seedling and will shortening the time for the tree to mature before final harvest.

E. Biochemical

The use of compressed dormancy could be applied to plants that go through an annual dormancy process. It is envisioned that numerous other plants with biochemical properties can be grown under this system.

VII. A UNIQUE PROCESS FOR ACCELERATING THE GROWTH CYCLE OF *Taxus* x *media* "Hicksii"

Based on previous discussion, we have developed a unique process for accelerating the growth of *Taxus* x *media* "Hicksii" which involves:

A closed loop commercially viable growing system using Compressed Dormancy. Our process will incorporate a closed loop growing system that will utilize field grown stock plants, cold chambers and greenhouses for growth of the plant.

A controlled growth environment including artificial lighting, $CO_2$ enhancement, ebb and flow floodable movable benches for watering, and heated greenhouses and cold chambers for enhanced plant growth. This uniquely developed growing process will produce a quality controlled product that is uniform and consistent.

These additional factors complement and increase the results reported above, with regard to Compressed Dormancy. Such methods are related to and described in previous submissions to the U.S. Patent Office (9,10) by the applicants.

The following discussion of the entire process is contained in six sections including; A) Plant Cuttings, B) Rooting, C) Greenhouse Description, D) Growing Cycle, E) Processing, F) Taxol Yield.

A. Plant Cuttings

1. Obtain cuttings from *Taxus x media "Hicksii"*. In the U.S. cuttings will be taken from open fields from late summer into early winter depending on the ability to access good plant material from field grown stock.

2. Softwood cuttings should be taken at the field site approximately 8 inches in length. The cuttings should be taken from the ends of the branches and contain a part of the previous seasons hardwood growth if possible. The amount of cuttings that can be obtained from shrub to shrub will vary depending on the size of the plant. The live cuttings then have to be packed on a daily basis and shipped back to the propagating facility.

Packing can be accomplished by taking bundles of 25–50 live cuttings, placing a rubber band around them, placing the cuttings in layers of 500–1,000 in a Styrofoam or corrugated box, covering each layer with damp burlap or spaghmum moss, and sealing each box and shipping them overnight express to the facility. Each box should contain 5,000–10,000 cuttings.

3. The area where the plants are prepared is commonly referred to those in the field of horticulture as a headhouse. At the headhouse facility each box of cuttings would be unpacked and readied for the propagating process. The area where this takes place should be as clean and sterile as possible. Workers should have on sterile overalls and wear disposable surgical masks and gloves. The workers would not be allowed to have food or drinks in this area and smoking would not be allowed at all anywhere in the complex.

The softwood cuttings would be unbundled, trimmed of needles on the lower 2 inches of the cutting, dipped in a solution of distilled water containing a disinfectant (clorox or equivalent) to prevent bacteria or fungal growth, dipped in a solution of root-inducing chemical (indolebutyric acid "IBA" brand name DIP'N GROW by Astoria-Pacific Inc) to promote quick root growth. Once this is accomplished the cuttings are then ready to be place into the growing container and ultimately into the greenhouse propagating facility.

Note: Any cuttings that are not processed should be unpacked from the shipping container and placed in trays single layer deep covered with moist burlap and placed in a cool storage locker with high relative humidity 80–90% at a temperature of 40 degrees. This will keep the cuttings alive until they can be processed.

B. Placing of Cutting into Rooting Container and Growing Bench

1. The rooting or growing container shall consist of a plastic pot approximately 1.5Δ×1.5Δ×6Δ in size or a plug tray (a plastic tray with numerous cells that are connected with one another in a tray configuration) of approximately the same dimensions. There will be slits in the bottom and sides of the container so as to allow for adequate drainage. There will be a minimum of 36 plants per square foot.

2. The growing container shall be filled with a soilless mix containing a 2:2:1 mixture of Canadian sphagnum peatmoss, horticultural vermiculite, horticultural perlite with a trace of washed sand (Brand name Metro Mix 200 Plant Propagating formula by Grace Sierra). The soilless mix has been sterilized and repacked by the manufacturer in 3 cubic foot plastic bags. One bag will fill approximately 216 pots. This material is used to hold the cutting in place during the formation of roots and to prevent the plant roots once formed from drying out.

3. The prepared cuttings will be inserted into the growing media within the pot to a depth of 2 inches. The pots are than placed pot to pot or flat to flat onto a movable Ebb and Flow bench (referred hereafter as the "bench") that will allow for a minimum of 36 plants per square foot.

4. The movable bench is 6"×17" in size. Other sizes are available depending on the width of the greenhouse. It is constructed in a manner that will allow the bench, when placed into the proper position within the greenhouse, to be flooded with water so as to water the plants from the bottom of the pot (Midwest GROmaster Inc.). A capillary effect will occur that will allow the water or fertilizer solution to be taken up into the pot through the slits in the sides and bottom of the pots.

The bench will then drain out and allow the plants to dry out until the next cycle. Timing of the flooding and draining will depend on the amount of root mass. The cycle in the beginning will be further apart (one time a day) and near the end (three to four times a day) closer together.

Once all the growing containers have been properly placed onto the bench, the bench can than be moved by a rail network system or otherwise into the greenhouse growing area.

C. Greenhouse Complex Description

1. Greenhouse Structure: The Greenhouse consists of 36" wide by 10" high by 210" long bays (VanWingerdon Greenhouse). The construction of the greenhouse frame is a galvanized 8 inch truss system held in place by 3 inch square steel poles spaced 10 foot on center. Each truss has 3 hoops that cover the 36 foot span. The entire greenhouse is covered with a double layer of 6 mil plastic that is inflated with air to provide a gap for insulating purposes and to provide the greenhouse with a tight outer covering so it will not rip under difficult weather conditions. There would be 7 bays giving a total square footage of 45,360.

Note: Greenhouses in the New Jersey area are installed in a configuration that locates the vent system on the west side of the building and the fan system on the east side. The reason for this is to take advantage of the prevailing winds for ventilation and cooling and to obtain maximum advantage of the sun for natural lighting during the winter months.

2. Floor Covering: The floor of the greenhouse is covered by a layer of 3,000 lb. concrete to provide for a level work area and an area that can be sterilized during each crop.

3. Heating system: First, in the area directly under the growing bench, small diameter (1 inch) aluminum fin pipes are spaced at an even distance of approximately 1 foot on center (DuoFin by BioTherm Inc.). Hot water is piped from a hot water boiler (Hydropulse) throughout the system to provide for a radiant heating system at the floor level. The temperature can be maintained within a close range (+/−2 degrees F) once the system has been in operation. By providing the heat underneath the bench, the system will then maintain the proper temperature at the base of the plant where rooting of the plant takes place.

The second type of heating occurs above the ground area and is accomplished by a hot air delivery system. An 18 inch 6 mil plastic tube with 2 inch holes punched at intervals of one foot in the sides deliver the heat to the air above the plants. These tubes are located above the truss and run from each end of the greenhouse to the middle of the greenhouse through the middle hoop. The hot air is produced by 2 small hot air furnaces (Reznor) located in each bay and mounted above the truss level.

Fuel for the above system can be provided by oil, natural gas or propane. The desired system would be either natural gas or propane. The temperature at the root zone area should be maintained between 60 and 70 degrees F around the clock until rooting occurs. The night time air temperature can be cooler and maintained at a minimum of 55 degrees F if possible. Day time air temperatures can be warmer than the root zone temperatures but not greater than a maximum of 80 degrees F if possible.

4. Ventilation: Due to the buildup of heat during the daytime within the greenhouse it is somewhat harder to maintain a steady 55 degrees F. Cooler temperatures can be maintained within the greenhouse due to the seasons that the greenhouse complex will be operating under (late autumn through spring). The day time air temperature can be maintained by the blending in of air from the outside from properly sized belt driven fans (located on the east end of the greenhouse) drawing air through vents (located at the west end).

If additional day time cooling is necessary a cool cell system can be installed at the end of the greenhouse where the vents open up to the outside air. The cool cell system utilizes evaporative cooling as the principal means of achieving the desired air temperature. Water is dripped over fiberboard mats. Air is than drawn through the mats by the fans. This actions produces a net ambient temperature drop of between 10 to 20 degrees.

5. Carbon Dioxide: CO2 is produced by the burning of natural gas in what is commonly called a CO2 generator (Johnson CO2 Generators). The CO2 will be used to enhance the growth of plants and is produced primarily during the day (or evening when artificial lighting is applied) when the levels of natural background CO2 drop off due to the greenhouse ventilation system being closed. Natural background levels of CO2 are around 300 ppm. Because of the high volume of plants within the greenhouse it is necessary to maintain the level of CO2 at 2 to 4 times the ambient level (600–1,200 ppm).

The addition of CO2 will only take place while the plant is in the photosynthetic mode. CO2 will not be added when the temperature in the greenhouse is sufficient to cause the ventilation system to allow outside air into the greenhouse or during the resting or dark period. A CO2 meter (Siemans controller) is hooked up to the CO2 generators and controls the operation of the units.

6. Artificial Lighting: A novel approach not currently being used in the propagating of yews is the use of artificial lighting. Lighting is critical to plant growth especially during the winter months. Since it is the desire of the researchers to produce as large a plant in the shortest amount of time it is necessary to use artificial lighting. The lights would be used to maintain a steady growing condition throughout the crop cycle of up to 16 hours a day. The timing of the lights would correspond to the season.

For example, during the spring and autumn the lights would only be needed for approx. 4–6 hours a day. During the winter the lights may be needed for 6–8 hours a day. During cloudy days the lights may be needed for the entire 16 hours. The duration of entire day would be maintained from 6 AM until 10 PM with a dark rest period for the plants from 10 PM to 6 AM.

The type of light that would be used is a 400 watt high pressure sodium vapor fixture (P. L. Light Systems Canada Inc. model #PL90M). The desired intensity would be maintained at approximately 75 micromoles/meter2/secPAR.

7. Movable EBB and FLOW benches: As described in the previous section a system of movable benches will be utilized within the greenhouse. The plants in the flats will be placed onto the movable benches and rolled via a pipe rail system into the greenhouse complex at one end of the greenhouse. The 17"×6" benches would than be rolled into each 36" bay leaving a 2" isle in the middle. The entire bay would be filled with the desired amount of benches. Once in place, the watering and drainage system would be hooked up.

8. Fertilizer and primary watering system: A Number of 500 gallon bulk storage tanks will be utilized for the bench watering and irrigation system. Some tanks will have just plain water and some a stock solution of water and water soluble fertilizer (Peters Fertilizer). Plain water will be utilized in the beginning of the propagation of the plants until the formation of the primary and secondary roots. At that point the fertilizer solution would be used for the duration of the cropping cycle.

Timers will be used to trigger the pumps to fill the benches. The benches have an automatic float device that will shut off the water so as not to overflow the sides of the bench. The water or fertilizer solution will remain within the bench for 3–5 minutes after filling. At that time the bench will automatically drain itself.

The drain from each bench will go to a common sump area where the unused solutions will be returned to the main storage tanks. This system recycles the solution for further use. A screen in each sump prevents the accumulation of any dirt or garbage from entering the main tank. At the end of each crop harvest the entire system would be sterilized to prevent the advent of any disease or fungal growth.

A good well-balanced water soluble fertilizer, consisting of a mix of 20% nitrogen, 20% phosphorus, and 20% potassium would be utilized and maintained at a rate of 20 ppm of Nitrogen in the solution. The pH of the solution should be maintained at the desired level of 6.0.

9. Relative Humidity: Control of humidity can be accomplished via an overhead misting system located in the truss system of the greenhouse or via an automatic overhead robotic water device. (ITS Grower Jr. by McConky Inc. or Grow International Inc.) Either device would spray a fine mist of water vapor above the plants to maintain the relative humidity at 80–90%. The misting cycle would be controlled by a humidity measuring device that would be hooked into the control system of the misting device.

D. Growing Cycle

The growing cycle of the plants is approximately two years. The following is an example of the sequence of events that could occur with the addition of the Compressed Dormancy process:

Primary Growth Cycle (9 months & 15 days)

1. September 15–October 15: Take cuttings from selected *Taxus* x *media* "Hicksii" and ship to greenhouse complex.

2. October 16–October 31: Prepare plant cuttings and move plants to greenhouse propagating area.

3. November 1–November 15: All plants should now be into the greenhouse growing area.

4. November 16–January 31: Primary root formation should have taken place by the end of January. This is a period of slow growth. The plants will be misted throughout the day and not fertilized. The flooded bench system will only be utilized when the soil moisture in the pot reaches a level that is slightly dry to the touch. CO2 would be utilized. Light levels are at their lowest and use of artificial lighting would be a necessity. It is critical to maintain a steady temperature under the movable benches to promote good root growth.

5. February 1–February 28: Formation of secondary root formation. During this period a slight increase in growth is expected. Fertilizer can now be added to the flooding cycle. It is still desirable to maintain the misting system. Lighting and CO2 would continue to be used. It is critical to maintain a steady temperature under the movable benches to promote good root growth.

6. March 1–June 30: This is the period of highest growth. The amount of watering would increase during this duration from one time a day to probably three times a day. Misting would continue. The addition of CO2 would continue. Light levels are at their highest and the addition of artificial lighting would diminish. Heating is still a must on cool nights and should continue until the outside air temperatures are maintained at approx. 65 degrees F. At this point we have a fully mature seedling or young plant with a developed primary and secondary root system, full stem, needles and terminal and side growing buds.

Compressed Dormancy Cycle (12 months & 15 days)

7. July 1–July 15 of the following year: During this period a systematic method of cold treatments and harvesting of the plants would occur. The method would utilize cold treatments to break the dormancy period within the plant, followed by a forced growing period within the greenhouse. This would occur in 60–75 day growing cycles. Thirty days within cold treatment and thirty to forty-five days under accelerated growth conditions. This integrated closed loop dormancy process would include the following steps.

a. After 30–45 days of growing the plants in a greenhouse, the flats containing the plants would be temporarily removed from the flooded bench. The worker would trim any roots that are coming out of the slits in the sides of each cell. The root material would be collected and stored in a cooler at 33–40 degrees F with a relative humidity of 75–95% until the processing step (See processing Section E below).

b. Next the worker would take the top 2–4 inches off each plant. The green needle clippings would be collected and stored in a cooler at 33–40 degrees F with a relative humidity of 75–95% until the processing step (See processing Section E below).

c. The flats containing the plants would be placed back onto the movable benches and moved into a cool storage area, such as a walk in cooler, to initiate the growth cycle. The plants would be exposed to no light conditions and kept at 33–40 degrees F with a relative humidity of 75–95% for thirty days. Moisture levels with the soil would be kept at a minimum. Fertilizer would be cut off.

d. After 30 days the plants are moved back into the greenhouse. Artificial lighting and CO2 would be used as described in the previous sections. During that time the amount of Nitrogen fertilizer would be doubled. This process of forcing the plant from a dormant non-growing period to an active growing condition will cause the plant to send out many numerous stems from the area previously trimmed.

At the end of the 30 to 45 day growing period the worker would take the top 2–4 inches off each plant. The green needle clippings would be collected and stored in a cooler at 33–40 degrees F with a relative humidity of 75–95% until the processing step. The entire movable bench would be disconnected from its water supply and moved back into the cool storage area to start the 30 day dormancy period all over again. These periods of alternating dormancy and accelerated growing are continued for one year until July 15, to provide for five growing cycles within that time period. The actual dates are stated below in TABLE A.

TABLE A

Cycle #1
Cold Treatment—July 1 to July 30
Accelerated Growing—August 1 to September 15
Clipping: September 15
Cycle #2
Cold Treatment—September 16 to October 15
Accelerated Growing Cycle—October 16 to November 30
Clipping: November 30
Cycle #3
Cold Treatment—December 1 to December 31
Accelerated Growing—January 1 to February 15
Clipping: February 15
Cycle #4
Cold Treatment—February 16 to March 15
Accelerated Growing—March 16 to April 30
Clipping: April 30
Cycle #5
Cold Treatment—May 1 to May 31
Accelerated Growing—June 1 to July 15
Clipping and harvest of entire plant: July 15

Final Harvest of Plants

8. July 15: This is the date for the start of the final harvesting of the entire plant.

a. First, the flats containing the plants would be temporarily removed from the flood bench. The worker would trim any roots that are coming out of the slits in the sides of each cell. The root material would be collected and stored in a cooler at 33–40 degrees F with a relative humidity of 75–95% until the processing step.

b. Next the worker would take the top 2–4 inches off each plant. The green needle clippings would be collected and stored in a cooler at 33–40 degrees F with a relative humidity of 75–95% until the processing step.

c. The flats containing the plants would be placed back onto the movable benches and left in the greenhouse for the next 10 days. During that time the amount of Nitrogen fertilizer would be doubled. At the end of the 10 day period the entire movable bench would be disconnected from its water supply and moved back into the headhouse area for processing. This cycle of trimming and harvesting would be conducted in blocks of 36'×100" until the entire greenhouse area is emptied.

d. Five percent of the total crop is not sent to the processing plant but is planted into an outside nursery area or field for use as stock plant material for the future to maintain a closed loop process.

9. July 30: Harvest all the plants from the greenhouse growing area then clean and ready the greenhouse growing area for the next growing cycle. The process has now reached the point where it will be self sustaining due to this closed loop process (See FIG. 2).

E. Processing

Processing of the whole plants would take place in the headhouse area and would utilize the following steps.

1. The flats would be unloaded from the movable benches and taken to the washing station where the plants are removed from the flats. The workers would wash off the base of the plant removing any soil and place the cleaned plant onto a conveyor belt that would take it to the next processing area.

The flats and movable benches would then be taken to the sterilization area where they would be washed with boiling water. Once clean the benches and flats would be stored in a clean area and are ready for use again.

2. The next step would be to remove the green leaf area of the plant from the lower stem and roots. This can be easily accomplished by clipping the plant approximately 1–2 inches from the base of the stem where the roots start.

The green leaf part of the plant is than collected and combined with the green needle plant clippings previously taken (If applicable, a separate processing step could occur for just the dormancy cycle from July 1 to April 30 in Growing Section D-7 above).

The roots and stem clippings are combined with the root clippings taken previously taken (If applicable, a separate processing step could occur for just the dormancy cycle from July 1 to April 30 in Growing Section D-7).

3. The green material is then placed into a stainless steel basket container (18 inches by 3 feet with 1/8 inch mesh). The basket is placed into a 2"×4" stainless drum and exposed to Liquid Nitrogen for approximately 1 minute. The basket is quickly taken and emptied into a shredding machine where the material is ground into small fragments. The material is then placed into 55 gal. stainless steel drums and sent to the processing plant.

The same process is done for the non-green root and stem material. The reason for the separation of the material is the fact that it is harder to extract the Taxol from material containing chlorophyll.

4. At the processing plant, the actual extraction of the Taxol from the biomass is a separate known process and will not be discussed at this time.

F. Estimate of amount of Taxol from above process.

The amount of Taxol that can be obtained from one acre of greenhouse using the above process is estimated to be approximately 25 Kg. (See Appendix A). To obtain that amount of Taxol from the wild would require the cutting of approximately 119,000, 10 inch, 80 year old Pacific Yew trees. The improvement of the invention over the current accepted standard is clearly obvious and novel.

VIII. FOOTNOTES

1. Hartzell Jr., H, The Yew Tree a Thousand Whispers, Hulogosi, 1991.

2. "Taxol-Background Information", *American Cancer Society Cancer Response System*, Bulletin #5290, May 11, 1993.

3. "FDA Approves Taxol for Therapeutic Use", *C&EN*, Jan. 11, 1992.

4. See footnote 1.

5. "The Loving Yew", Zelenka Nursery, Inc. Pamphlet, 1992.

6. Hartman, H. T., Kester, D. E., *Plant Propagation Principals and Practices*, Second Edition, Prentise Hall, 1968, pp. 506–519.

7. J. Janick, *Horticultural Science*, second Edition, W. H. Freeman and Company, 1972, pp. 156–157.

8. McCann, K. R. "Yews in the News", Greenhouse Grower, January 1992, page 38.

9. U.S. patent application Ser. No. 08/304,587 filed Sep. 12, 1994, "Integrated Closed Loop Method for Accelerating the Growth of Yew Biomass and Increasing the Production of Yew Biomass for the Extraction of Taxol and Other Compounds."

10. U.S. patent application, Ser. No. 08/061,992 filed May 17, 1993, "A Method for Accelerating the Growth of Plants and Increasing the Production of Taxol and Other Compounds."

APPENDIX A

Assumptions for illustration below

- 4.00 grams (0.01 Kg) fresh weight per clipping of needles
- 55.00 grams (0.06 Kg) per plant fresh weight at final harvest
- 2.50 Kg Taxol per 45,400 Kg fresh weight of plant clippings
- 5 Times as much Taxol in whole plant as in clippings
- 36 Plants per square foot
- 43,560 Square feet per acre of greenhouse under cover Illustration assumes that there is a harvest of all plants with no fatalities Crop 1–4 are clippings, crop 5 is the final harvest of whole plant seedling

| Plants/ Acre | September 15 Crop 1 Kg Clippings | November 30 Crop 2 Kg Clippings | February 15 Crop 3 Kg Clippings | April 30 Crop 4 Kg Clippings | July 15 Crop 5 Whole plant |
|---|---|---|---|---|---|
| 1,568,160 | 6,273 | 6,273 | 6,273 | 6,273 | 86,249 |

| Final Harvest numbers | Kg biomass | Kg Taxol | Patients |
|---|---|---|---|
| Clippings | 25,091 | 1.38 | 691 |
| Whole plant | 86,249 | 23.75 | 11,873 |
| Total Kg of Taxol produced | | 25.13 | |
| Total Pounds of Taxol produced | | 55.28 | |
| Total estimated # of patients treated | | | 12,564 |

Note
118,735 10" diameter Pacific Yew trees that need to be cut to = 1 acre of greenhouse grown Taxol biomass (3)

What is claimed is:

1. A method of growing, harvesting, and processing the plant *Taxus X Media* 'Hicksii' and related Taxus species, comprising the steps of:

a) planting plant cuttings of said plant in a growing media in a greenhouse to propagate said plants;

b) harvesting a part of each of said plants after the formation of the primary and secondary root systems have taken place;

c) processing said harvested plant parts to extract Taxol or Taxotere from said plant parts;

d) placing the remaining unharvested plants in a cool storage area for 20 to 40 days to initiate the growth cycle, wherein the temperature is maintained at 33 to 40 degrees F, and the relative humidity is maintained at 75 to 95%, and lighting is maintained for less than 8 hours per day;

e) removing said unharvested plants from said cool storage area and returning said plants to said greenhouse for 20 to 40 days of growth;

f) harvesting a part of each of said unharvested plants;

g) processing said harvested plant parts of step (f) to extract Taxol or Taxotere from said plant parts;

h) again placing said unharvested plants in a cool storage area for 20 to 40 days to again initiate a new growth cycle, wherein the temperature, relative humidity, and lighting are maintained as in step d) above;

i) removing said unharvested plants from said cool storage area and returning said plants to said greenhouse for 20 to 40 days of growth;

j) harvesting and processing a part of each of said plants as recited in steps f) and g) above;

k) repeating steps h), i), and j) above at least one more time;

l) harvesting all of said plants;

m) processing a predetermined number of said harvested plants to extract Taxol or Taxotere from the entire plant; and n) transplanting the remaining harvested plants outside of said greenhouse to grow additional stock to provide a source of new plant cuttings to transplant into said greenhouse.

2. A method in accordance with claim 1, wherein the step m) of processing includes processing the entire plant, including the roots, the heart wood, the branches, the main stem, the needles, the bark, or the seeds.

3. A method in accordance with claim 1, step (a), wherein said plant cuttings are rooted.

4. A method in accordance with claim 1, step (a), wherein said plant cuttings are unrooted.

5. A method in accordance with claim 1, wherein the step of transplanting includes replanting said harvested plants in a managed field setting.

6. A method in accordance with claim 1, wherein the step of transplanting includes replanting said harvested plants in a natural setting for reforesting.

7. A method in accordance with claim 1, wherein the step of transplanting includes replanting said harvested plants in another greenhouse.

8. A method in accordance with claim 1, further including the steps of:

a) controlling the temperature of said greenhouse to maintain said growing media at a temperature of 55 to 80 degrees F;

b) maintaining the relative humidity of the atmosphere in said greenhouse between 75% and 95%;

c) providing artificial lighting in said greenhouse to extend the time of natural light up to 16 hours per day, with an intensity of at least 50 micromoles/meter2/sec/PAR;

d) enriching the atmosphere in said greenhouse with carbon dioxide at a level of 600 ppm to 1200 ppm;

e) providing a water-soluble fertilizer for said plants; and f) maintaining the soil with a pH between 5.5 and 6.0 for said plants.

9. A method in accordance with claim 1, wherein the step of planting plant cuttings in said greenhouse includes the steps of washing the base of said plant cuttings in distilled water and dipping the cuttings into a root-inducing chemical.

10. A method in accordance with claim 8, wherein controlling the temperature of said growing media includes the step of using a hot water system to maintain said growing media at said temperature of 60 to 70 degrees F and using a hot air system to maintain an air temperature of 55 to 80 degrees F in said greenhouse.

11. A method in accordance with claim 1, wherein the step of harvesting includes the use of a 6"×12–17" movable benches for moving the plants from the growing area to a harvest station.

12. A method in accordance with claim 1, further including the step of using hydroponics to fertilize said plant cuttings.

13. A method in accordance with claim 1, further including the use of a movable 6"×12–17" ebb and flood bench as a means of supporting said plants and for mechanized transporting to a harvest station.

14. A method of growing and harvesting the plant *Taxus X Media* 'Hicksii' and related Taxus species, comprising the steps of:

a) planting plant cuttings of said plant in a growing media in a greenhouse to propagate said plants;

b) harvesting a part of each of said plants after the formation of the primary and secondary root systems have taken place;

c) placing the remaining unharvested plants in a cool storage area for 20 to 40 days to initiate the growth cycle, wherein the temperature is maintained at 33 to 45 degrees F, and the relative humidity is maintained at 75% to 95%, and lighting is maintained for less than 8 hours per day;

d) removing said unharvested plants from said cool storage area and returning said plants to said greenhouse for 20 to 40 days of growth;

e) again placing said unharvested plants in a cool storage area for 20 to 40 days to initiate the growth cycle again, wherein the temperature, relative humidity, and lighting are maintained as above;

f) removing said unharvested plants from said cool storage area and returning said plants to said greenhouse for 20 to 40 days of growth;

g) repeating steps c), d), and e) above at least one more time; and h) harvesting and transplanting all of said plants.

15. A method in accordance with claim 14, wherein the step of transplanting includes replanting said harvested plants in a managed field setting.

16. A method in accordance with claim 14, wherein the step of transplanting includes replanting said harvested plants in a natural setting for reforesting.

17. A method in accordance with claim 14, wherein the step of transplanting includes replanting said harvested plants in another greenhouse.

18. A method in accordance with claim 14, wherein the step of transplanting includes replanting to allow for the later harvesting of the entire plant.

19. A method in accordance with claim 14, wherein the step of transplanting includes replanting to allow for the later harvesting of any part of the plant including fruit or nut.

* * * * *